US006797743B2

(12) United States Patent
McDonald et al.

(10) Patent No.: US 6,797,743 B2
(45) Date of Patent: Sep. 28, 2004

(54) ANTIMICROBIAL POLYMER

(75) Inventors: William F. McDonald, Utica, OH (US); Stacy C. Wright, Flint, MI (US); Andrew C. Taylor, Ann Arbor, MI (US)

(73) Assignee: Michigan Biotechnology Institute, Lansing, MI (US)

( * ) Notice: Subject to any disclaimer, the term of this patent is extended or adjusted under 35 U.S.C. 154(b) by 270 days.

(21) Appl. No.: 09/850,324

(22) Filed: May 7, 2001

(65) Prior Publication Data

US 2003/0220467 A9 Nov. 27, 2003

Related U.S. Application Data

(63) Continuation-in-part of application No. 09/671,784, filed on Sep. 27, 2000, now Pat. No. 6,399,714, and a continuation-in-part of application No. 09/698,679, filed on Oct. 27, 2000, now Pat. No. 6,495,657.

(51) Int. Cl.[7] .............................................. C08K 3/08
(52) U.S. Cl. ...................... 523/122; 524/403; 524/413; 524/434
(58) Field of Search .......................... 523/122; 524/403, 524/413, 434

(56) References Cited

U.S. PATENT DOCUMENTS

| 3,695,921 A | 10/1972 | Shepherd et al. |
| 4,054,139 A | 10/1977 | Crossley ..................... 128/260 |
| 4,128,633 A | 12/1978 | Lorenz et al. |
| 4,217,338 A | 8/1980 | Quash |
| 4,302,368 A | 11/1981 | Dudley et al. |
| 4,310,509 A | 1/1982 | Berglund et al. |
| 4,323,557 A | 4/1982 | Rosso et al. |
| 4,357,476 A | 11/1982 | Reincher et al. |
| 4,419,444 A | 12/1983 | Quash |
| 4,442,133 A | 4/1984 | Greco et al. |
| 4,581,028 A | 4/1986 | Fox, Jr. et al. ................. 623/2 |
| 4,603,152 A | 7/1986 | Laurin et al. ............... 604/265 |
| 4,605,564 A | 8/1986 | Kulla et al. |
| 4,642,104 A | 2/1987 | Sakamoto et al. |
| 4,675,347 A | 6/1987 | Mochizuki et al. |
| 4,678,660 A | 7/1987 | McGary et al. |
| 4,720,512 A | 1/1988 | Hu et al. |
| 4,786,556 A | 11/1988 | Hu et al. |
| 4,865,870 A | 9/1989 | Hu et al. |
| 4,933,178 A | 6/1990 | Capelli ........................ 424/78 |
| 4,987,181 A | 1/1991 | Bichon et al. |
| 4,999,210 A | 3/1991 | Solomon et al. |
| 5,019,096 A | 5/1991 | Fox, Jr. et al. ................. 623/1 |
| 5,049,684 A | 9/1991 | Tomibe et al. |
| 5,069,907 A | 12/1991 | Mixon et al. |
| 5,316,912 A | 5/1994 | Heimgartner et al. |
| 5,328,698 A | 7/1994 | Onwumere et al. |
| 5,344,411 A | 9/1994 | Domb et al. |
| 5,405,919 A | 4/1995 | Keefer et al. |
| 5,641,855 A | 6/1997 | Scherr et al. |
| 5,650,447 A | 7/1997 | Keefer et al. |
| 5,707,366 A | 1/1998 | Solomon et al. ............. 604/265 |
| 5,709,672 A | 1/1998 | Illner |
| 5,762,638 A | 6/1998 | Shikani et al. |
| 5,962,520 A | 10/1999 | Smith et al. |
| 6,030,632 A | 2/2000 | Sawan et al. ................ 424/405 |
| 6,042,877 A | 3/2000 | Lyon et al. .................. 427/2.31 |

(List continued on next page.)

FOREIGN PATENT DOCUMENTS

| EP | 0 882 461 | 12/1998 | |
| EP | 0 969 056 | 1/2000 | |
| GB | 2 084 466 | 4/1982 | |
| GB | 2 153 235 | 8/1985 | |
| GB | 2 225 580 | 6/1990 | |
| JP | 11222402 | 8/1999 | |
| WO | WO 86/02561 | 5/1986 | |
| WO | WO 94/13870 | 6/1994 | |
| WO | WO 95/05400 | 2/1995 | |
| WO | 00/17254 | 3/2000 | ........... C08G/69/08 |
| WO | WO 01/11956 | 2/2001 | |

OTHER PUBLICATIONS

Patent Abstracts of Japan vol. 1999, No. 13, Nov. 30, 1999 & JP 11 222402 A (Osaka Gas Co. Ltd), Aug. 17, 1999 abstract.

PCT, International Search Report for PCT/US02/14304.

Satoh et al., "Immobilization of Saccharides and Peptides on 96–Well Microtiter Plates with Methyl Vinyl ether–Maleic Anhydride Copolymer", Anal. Biochem., 260, 96–102, 1998.

Vercruysse et al., "Synthesis and in Vitro Degradation of New Polyvalent Hydrazide Cross–Linked Hydrogels of Hyaluronic Acid", Bioconj. Chem., 8, 686–694, 1997.

O'Shannessy et al., Immobilization of Glycoconjugates by Their Oligosaccharides: Use of Hydrazido–Derivatized Matrices, Anal. Biochem., 191, 1–8, 1990.

(List continued on next page.)

Primary Examiner—Ana Woodward
(74) Attorney, Agent, or Firm—Foley & Lardner LLP

(57) ABSTRACT

A polymeric composition having antimicrobial properties and a process for rendering the surface of a substrate antimicrobial are disclosed. The polymeric composition comprises a crosslinked chemical combination of (i) a polymer having amino group-containing side chains along a backbone forming the polymer, (ii) an antimicrobial agent selected from metals, metal alloys, metal salts, metal complexes and mixtures thereof, and (iii) a crosslinking agent containing functional groups capable of reacting with the amino groups. In one example embodiment, the polymer is a polyamide formed from a maleic anhydride or maleic acid ester monomer and alkylamines thereby producing a polyamide having amino substituted alkyl chains on one side of the polyamide backbone; the crosslinking agent is a phosphine having the general formula $(A)_3P$ wherein A is hydroxyalkyl; and the metallic antimicrobial agent is selected from chelated silver ions, silver metal, chelated copper ions, copper metal, chelated zinc ions, zinc metal and mixtures thereof.

37 Claims, 4 Drawing Sheets

U.S. PATENT DOCUMENTS

| | | | |
|---|---|---|---|
| 6,056,967 A | | 5/2000 | Steuerle et al. |
| 6,087,462 A | | 7/2000 | Bowers et al. |
| 6,121,027 A | | 9/2000 | Clapper et al. |
| 6,153,724 A | | 11/2000 | Hollingsworth |
| 6,162,487 A | | 12/2000 | Darouiche |
| 6,217,780 B1 | * | 4/2001 | Denkewicz et al. ........ 210/764 |
| 6,224,579 B1 | | 5/2001 | Modak et al. |
| 6,232,336 B1 | | 5/2001 | Hrabie et al. |
| 6,232,434 B1 | | 5/2001 | Stamler et al. |
| 6,319,674 B1 | | 11/2001 | Fulcrand et al. |
| 6,340,465 B1 | | 1/2002 | Hsu et al. |
| 6,399,714 B1 | | 6/2002 | Huang et al. |
| 6,495,657 B1 | | 12/2002 | McDonald et al. |
| 6,509,104 B2 | | 1/2003 | Huang et al. |

OTHER PUBLICATIONS

Ito et al., Preparation of High Capacity Affinity Adsorbents Using New Hydrazino–Carriers and Their Use for Low and High Performance Affinity Cheomatography of Lectins, J. Biochem. (Tokyo), 99, 1267–1272.

Junowicz et al., The Derivatization of Oxidized Polysaccharides for Protein Immobilization and Affinity Chromatography Biochim. Biophys. Acta 428, 157–165, 1976.

Miron et al., Polyacrylhyrdazio–Agarose: Preparation via Periodate Oxidation and use for Enzyme Immobilization and Affinity Chromatography, J. Chromatogr., 215, 55–63, 1981.

Heimgartner, et al., Polyacrylic Polyhydrazides as Reagents for Detection of Glycoproteins, Anal. Biochem., 181, 182–189, 1989.

Fleminger et al., Oriented Immobilization of Peridate–Oxidized Monoclonal Antibodies on Amino and Hydrazide Derivatives of Eupergit C, Applied Biochem., 23, 123–137, 1990.

Del Rosso et al., Binding of the Basement–Membrane Glycoprotein Lamnin to Glycosaminoglycans, Biochem. J., 199, 699–704, 1981.

Henderson et al., Immobilised Phosphines Incorporation the Chiral Bioploymers Chitosan and Chitin, J. Chem. Soc., Chem. Commun., 9, 1863–1864, 1994.

Petach et al., A New Coupling Reagnet for the Covalent Immobilisation of Enzymes, J. Chem. Soc., Chem. Commun., 17, 2181–2182, 1994.

Cochrane et al., Application of Tris(hydroxymethyl) Phophine as a Coupling Agent for Alcohol Dehydrogenase Immobilization, Enzyme Microbial Technol., 18, 373–378, 1996.

Inman et al., Synthesis of Large Haptenic Compounds Having a Covalent Functional Group That Permits Convalent Linkage to Proteins, Cell Surfaces, Immunochemistry, 10, 153–163, 1973.

Ellis et al., Water–Soluble Tris(hydroxymethyl) Phospine Complexes with Nickel, Palladium, and Platinum, Inorg. Chem., 31, 3026–3033, 1992.

Lin et al., Preparation of Surface–modified Albumin Nanospheres, Biomaterials, V. 18, N. 7, 559–565, 1997.

Marconi et al., New Polyurethane Compsitions able to bond high Amounts of both Albumin and Heparin, V. 16, N. 6, 449–456, 1995.

Oswald et al., "Properties of a Thermostable B–Glycosides Immobilized Using Tris(hydroxymethyl) Phosphine as a Highly Effective Coupling Agent", Enzyme Microbial Technol., 23, 14–19, 1998.

Isosaki et al., Immobilization of Protein Ligands with Methyl Vinyl Ether–maleic Anhydride Copolymer, J. Chromatogr., 597, 123–128, 1992.

* cited by examiner

ANTIMICROBIAL POLYMER

CROSS-REFERENCE TO RELATED APPLICATIONS

This application is a continuation-in-part of U.S. Ser. No. 09/671,784, filed Sep. 27, 2000, Issued as U.S. Pat. No. 6,399,714, on Jun. 4, 2002; and this application is a continuation-in-part of U.S. Ser. No. 09/698,619, filed Oct. 27, 2000, issued as U.S. Pat. No. 6,495,657, on Dec. 17, 2002.

STATEMENT REGARDING FEDERALLY SPONSORED RESEARCH OR DEVELOPMENT

This invention was made with Government support under NREL Subcontract NO. XXE-9-29058-01, Prime Contract No, DE-AC36-98G010337 awarded by the Department of Energy. The Government has certain rights in this invention.

BACKGROUND OF THE INVENTION

1. Field of the Invention

This invention relates to a polymeric composition having antimicrobial properties and a process for rendering the surface of a substrate antimicrobial. The polymeric composition is a crosslinked chemical combination of (i) a polymer having amino group-containing side chains along a backbone forming the polymer, (ii) an antimicrobial agent selected from metals, metal alloys, metal salts, and metal complexes, and (iii) a crosslinking agent containing functional groups capable of reacting with the amino groups on the polymer.

2. Description of the Related Art

Many medical procedures involve the placement of medical devices, such as catheters, endotracheal tubes, prostheses, grafts, sutures, dressings and implants, in the human body. Infection is a common complication associated with the use of such medical devices. Accordingly, many research efforts have concentrated on finding means to prevent infection associated with these medical devices.

One solution to this infection problem has been the use of medical device coatings having metallic antimicrobial agents. An "antimicrobial" agent is an agent that has antiviral, antibacterial, and/or antifungal properties. (Antiviral means capable of killing, or suppressing the replication of, viruses. Anti-bacterial means bacteriostatic or bactericidal. Bactericidal means the killing of microorganisms. Bacteriostatic means inhibiting the growth of microorganisms. Antifungal means capable of killing or suppressing replication of fungi.) It has been particularly desirable to use a coating for implantable medical devices that is bacteriostatic, i.e., inhibits bacterial growth, such that the device can be implanted for longer periods without compromising the subject through a secondary bacterial infection. For example, U.S. Pat. No. 4,054,139 discloses a catheter coated with a silver-based material that reduces infection; U.S. Pat. No. 4,603,152 discloses a medical device coated with an antimicrobial composition including a polymeric binder and an antimicrobial metal compound such as a silver salt; U.S. Pat. No. 4,933,178 discloses a medical device having an antimicrobial coating comprising a polymeric material and a metal (e.g., silver, gold, zinc, platinum, copper) salt of sulfonylurea; and U.S. Pat. No. 5,019,096 discloses an infection resistant material used on medical devices which includes a polymeric component (e.g., polyurethane or silicone) and a silver salt.

Even though various medical device coatings having metallic antimicrobial agents are known, there is still a need for an improved antimicrobial polymer coating that may be easily applied to a substrate to provide an article which has excellent antimicrobial properties and which retains its antimicrobial properties in a permanent and non-leachable fashion when in contact with bodily fluids for prolonged periods. In addition, it would be beneficial if this coating could be combined with an anti-thrombogenic coating to prevent both clotting and bacterial infection. There is also a need for antimicrobial coatings that are useful in fields other than medical devices, such as antifouling applications for aqueous and marine environments, and corrosion control.

SUMMARY OF THE INVENTION

The foregoing needs are met by a polymeric composition having antimicrobial properties, wherein the polymeric composition comprises a crosslinked chemical combination of (i) a polymer having side chains along a backbone forming the polymer, at least two of the side chains containing an amino group, (ii) an antimicrobial agent selected from metals, metal alloys, metal salts, metal complexes and mixtures thereof, and (iii) a crosslinking agent containing at least two functional groups capable of reacting with the amino groups. An article according to the invention comprises a substrate and a coating of the polymeric composition disposed on at least a portion of the substrate.

The polymer used in the polymeric composition comprises a polymer having side chains along a backbone forming the polymer wherein at least two of the side chains contain an amino group ( —NRH, —NH$_2$, —NRH$_2^+$, —NH$_3^+$). In one example embodiment, the polymer is a polyamide having amino substituted alkyl chains on one side of the polymer backbone. The crosslinking agent used in the polymeric composition contains at least two functional groups capable of reacting with the amino groups of the polymer used in the coating. In one example of the crosslinking agent used in the polymeric composition, the crosslinking agent is selected from the group consisting of phosphines having the general formula (A)$_3$P, wherein A is hydroxyalkyl, and mixtures thereof. One more specific example of the crosslinking agent used in the polymeric composition is tris(hydroxymethyl)phosphine. Specific nonlimiting examples of the metallic antimicrobial agent used in the polymeric composition include chelated silver ions, silver metal, chelated copper ions, copper metal, chelated zinc ions, zinc metal and mixtures thereof.

An article having an antimicrobial surface may be produced by a process according to the invention in which a polymer having at least two amino substituted side chains is mixed with a metallic antimicrobial agent and a crosslinking agent to produce a polymer solution. The crosslinking agent contains at least two crosslinking functional groups which react and combine with amino groups on the polymer. The polymer solution is coated on at least a portion of a substrate to produce a crosslinked antimicrobial polymer coating on the substrate.

In an example embodiment of the invention, the versatile chemical methodology of the invention allows for the deposition of an antimicrobial polymeric composition on a polymeric substrate (e.g., polydimethylsiloxane, polyurethane, and polypropylene). The polymeric composition includes a two dimensional polymer having a backbone of repeating β-amino acid units with long aliphatic side-chain and free NH— and NH$_2$—substituents and may be synthesized by condensation of 2(5H)-furanone, or maleic acid derivatives (such as anhydride, esters, and so on) with a long-chain amine (e.g., tetradecylamine) and a polyamine (e.g., pentaethylenehexamine). Crosslinking of the two-dimensional polymer is undertaken with tris(hydroxymethyl)phosphine (the crosslinking agent) and a metallic antimicrobial agent such as chelated silver ions, silver metal, chelated copper ions, copper metal, chelated zinc ions, and zinc metal.

Experimental studies indicate that when chelated silver ions, silver metal, chelated copper ions, copper metal, chelated zinc ions or zinc metal are incorporated into the two-dimensional polymer and the polymer is crosslinked with the crosslinking agent, the resulting polymeric composition exhibits strong inhibitory activity against target pathogenic microorganisms. When the polymeric composition comprises: (a) first crosslinked chemical combination of (i) the polymer, (ii) a first antimicrobial agent selected from metals, metal alloys, metal salts, and metal complexes, and (iii) the crosslinking agent; and (b) a second crosslinked chemical combination of (i) the polymer, (ii) a second different antimicrobial agent selected from metals, metal alloys, metal salts, and metal complexes, and (iii) the crosslinking agent, a galvanic cell is formed between the two different metals or ions that provides synergistic antimicrobial activity greater than the sum of the activity of the individual metals or ions alone.

It is therefore an advantage of the present invention to provide an improved antimicrobial polymeric composition that may be easily applied to a substrate to produce an article which has excellent antimicrobial properties and which retains its antimicrobial properties in a permanent and non-leachable fashion when placed in an environment (e.g., bodily fluids) that may promote bacterial growth.

It is another advantage of the present invention to provide an improved antimicrobial polymeric composition that may be easily applied to a substrate for the prevention of medical device-related infections.

It is a further advantage of the present invention to provide an improved antimicrobial polymeric composition that may be easily applied to a substrate along with an anti-thrombogenic coating to prevent both clotting and bacterial infections.

It is yet another advantage of the present invention to provide an improved antimicrobial polymeric composition that may be easily applied to a substrate for antifouling applications for aqueous and marine environments.

It is still another advantage of the present invention to provide an improved antimicrobial polymeric composition that may be easily applied to a substrate for corrosion control coatings.

These and other features, aspects, and advantages of the present invention will become better understood upon consideration of the following detailed description, drawings, and appended claims.

DETAILED DESCRIPTION OF THE INVENTION

The present invention is directed to a polymeric composition having antimicrobial properties. The polymeric composition comprises a crosslinked chemical combination of (i) a polymer having side chains along a backbone forming the polymer, at least two of the side chains containing an amino group, (ii) an antimicrobial agent selected from metals, metal alloys, metal salts, metal complexes and mixtures thereof, and (iii) a crosslinking agent containing at least two functional groups capable of reacting with the amino groups. An article having a antimicrobial surface according to the invention comprises a substrate and a coating of the antimicrobial polymeric composition disposed on at least a portion of the substrate.

Figure 1A:
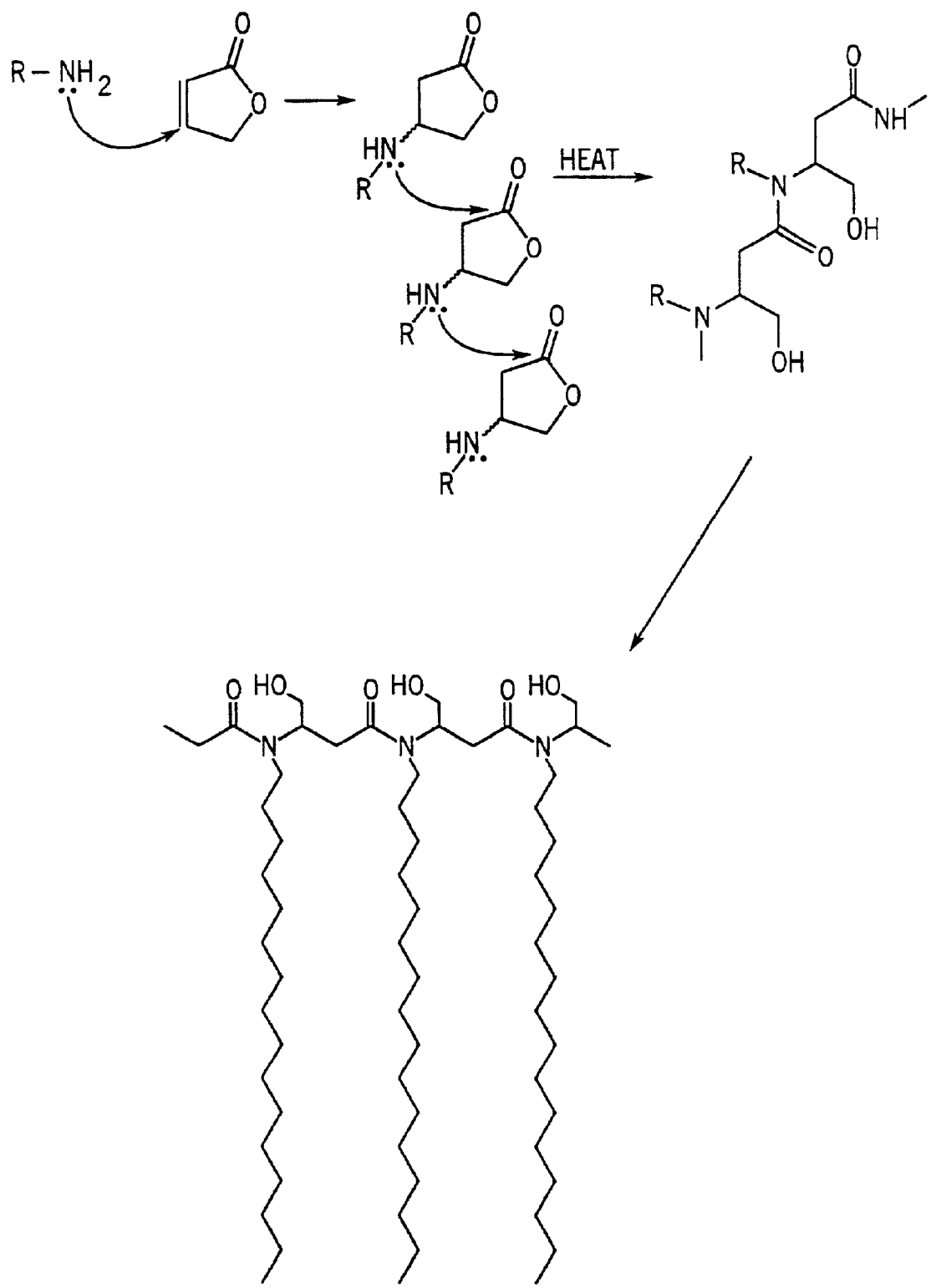
FIG. 1A shows a process for synthesizing a polyamide that is suitable for forming an antimicrobial polymeric composition coating in accordance with the present invention.
Figure 1B:
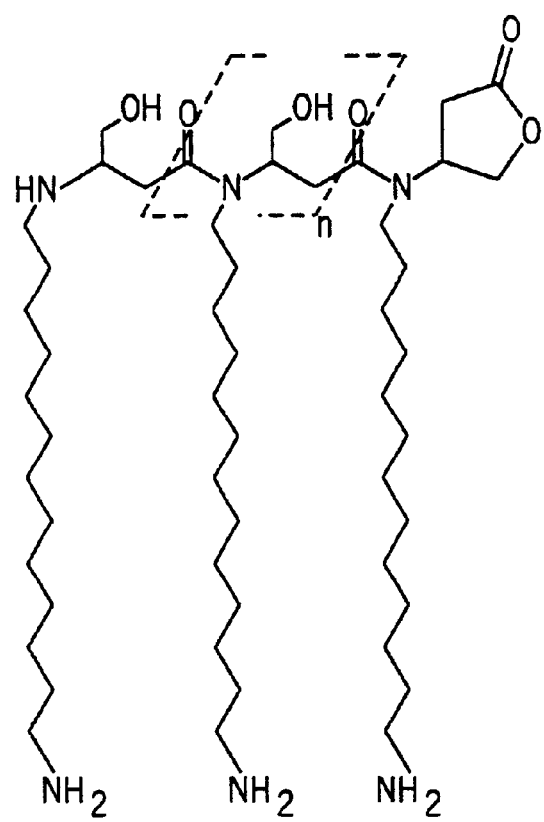
FIG. 1B shows example polyamides having amino groups that are suitable for forming the antimicrobial polymeric composition coating in accordance with the present invention.
Figure 1B:
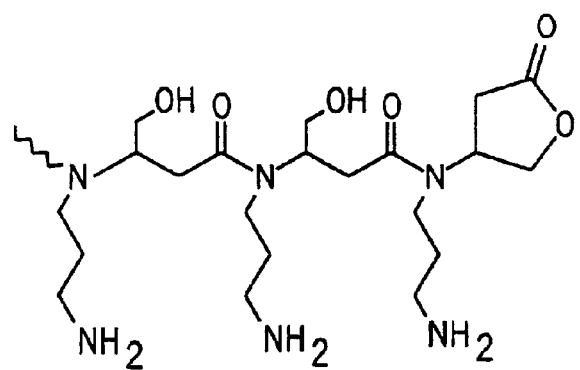

The polymer used in the antimicrobial polymeric composition comprises a polymer having side chains along a backbone forming the polymer wherein at least two of the side chains contain an amino group (—NRH, —NH$_2$, —NRH$_2^+$, —NH$_3^+$). In one example embodiment of the polymer, the polymer is a polyamide synthesized using the polymerization reactions disclosed in U.S. Pat. No. 6,153,724, which are shown in FIG. 1A. Looking at FIG. 1A, it can be seen that the polyamide can be synthesized using an $\alpha,\beta$-unsaturated gamma-lactone, such as 2(5H)-furanone, as an agent to effect the regular, sequential alignment of side chains along a polyamide backbone. The furanone undergoes facile reaction with a primary amine by Michael-type addition to yield $\alpha,\beta$-amino gamma-lactone which then polymerizes to form a polyamide chain with the pendant side chain. Depending on the side group (R), the method can produce many different types of polyamides. When the R group is a polyamine (such as pentaethylenehexamine), a polymer having alkyl chains on one side and amino substituted alkyl chains on the other side of the polymer backbone and hydroxymethyl groups on the other side of the backbone is formed. See FIG. 1B. This example two-dimensional polymer has a backbone of repeating $\beta$-amino acid units with fatty alkyl (tetradecyl) and polyamine (derived from pentaethylenehexamine) side chains randomly distributed along the chain. By virtue of its amphithetic properties, the two-dimensional polymers are easily soluble in both water and most organic solvents (e.g., alcohols, tetrahydrofuran, chloroform, toluene, N,N-dimethylformamide, and the like).

One polyamide disclosed in U.S. Pat. No. 6,153,724 and useful in the present invention is formed by reacting an $\alpha,\beta$-unsaturated lactone and a first amine to form an intermediate reaction product, wherein the first amine is selected from RR$_1$NH, RNH$_2$, RR$_1$NH$_2^+$, RNH$_3^+$ and mixtures thereof, wherein R and R$_1$ can be the same or different and each contain between about 1 and 50 carbon atoms and are optionally substituted with heteroatoms oxygen, nitrogen, sulfur, and phosphorus and combinations thereof; and (ii) reacting the intermediate reaction product and a polyamine to form the polyamide, wherein the second polyamine is selected from R$_2$R$_3$NH, R$_2$NH$_2$, R$_2$R$_3$NH$_2^+$, R$_2$NH$_3^+$ and mixtures thereof, wherein R$_2$ and R$_3$ can be the same or different and each contain an amino group (—NRH, —NH$_2$, —NRH$_2^+$, —NH$_3^+$) and between about 1 and 50 carbon atoms and are optionally substituted with heteroatoms oxygen, nitrogen, sulfur, and phosphorus and combinations thereof, wherein multiple of the R, R$_1$, R$_2$, and R$_3$ are in vertically aligned spaced relationship along a backbone formed by the polyamide. In one example embodiment of the invention, R, R$_1$, R$_2$, and R$_3$ may be selected from alkyl, alkenyl, alkynyl, cycloalkyl, aryl, aralkyl, hydroxyl, nitrile, carboxyl, sulfate, phosphate, sulfonyl, trialkylammonium and combinations thereof and optionally can be substituted with a halogen selected from the group consisting of chlorine, iodine, bromine, fluorine and combinations thereof. The R, $R_1$, $R_2$, and $R_3$ groups may be the same or different depending on the desired structure for the final polyamide. In other words, the first amine and the second amine used in the polymerization process may be the same or different.

Figure 2A:
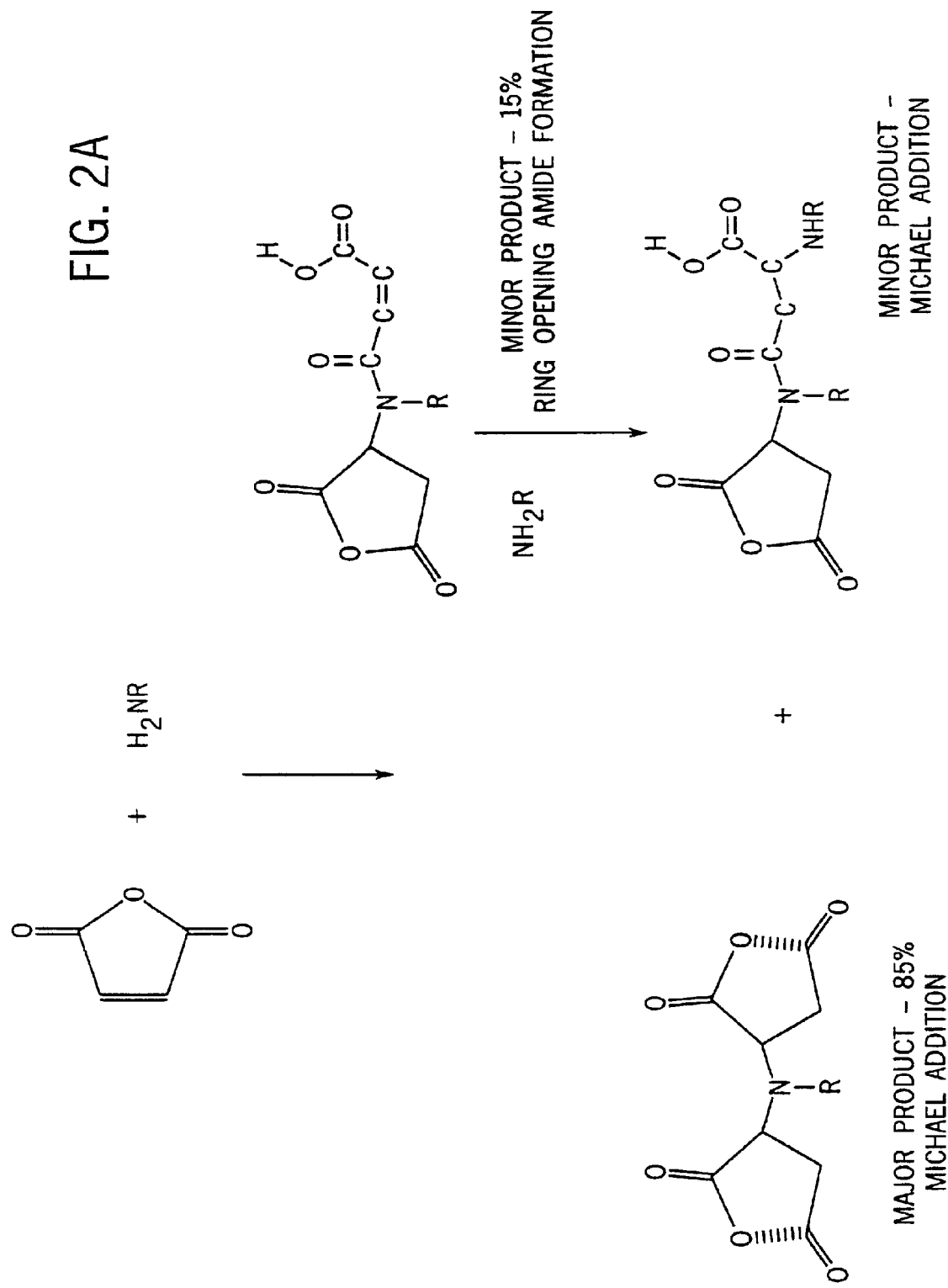
FIGS. 2A and 2B show a process for synthesizing another example polyamide having amino groups that are suitable for forming the antimicrobial polymeric composition coating in accordance with the present invention.
Figure 2B:
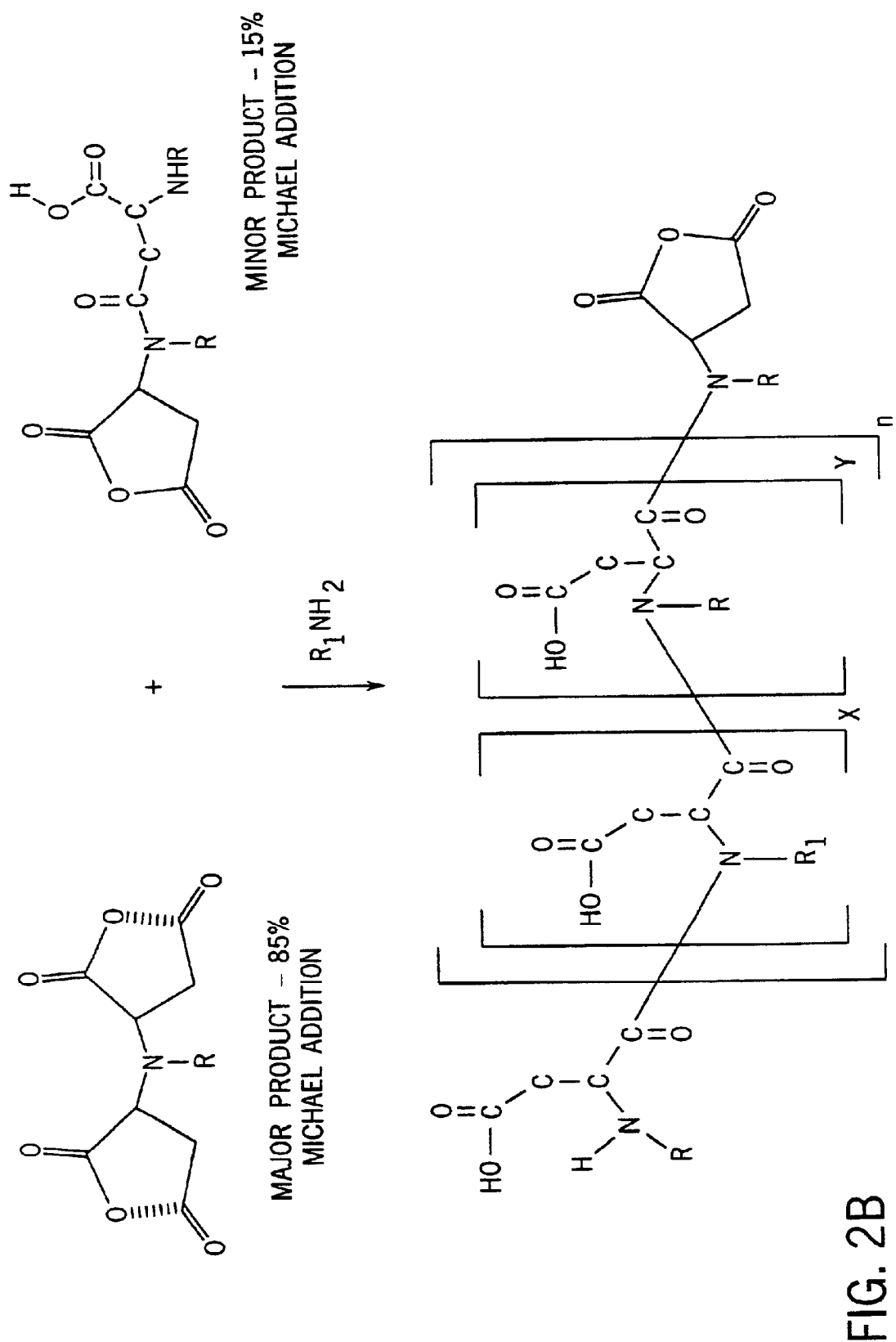

In another example of the polymer used in the antimicrobial polymeric composition, the polymer is a polyamide synthesized using the polymerization reaction disclosed in the U.S. patent application entitled "Two Dimensional Polyamides Prepared from Unsaturated Carboxylic Acids and Amines" filed on Oct. 27, 2000 by William F. McDonald et al., which is owned by the assignee of the present invention and is incorporated herein by reference. In the U.S. patent application, there is described a polymerization process in which a monomer selected from unsaturated carboxylic acids, esters of unsaturated carboxylic acids, anhydrides of unsaturated carboxylic acids, and mixtures thereof is reacted with a first amine to form an intermediate reaction product, and then the intermediate reaction product is reacted with a polyamine to form a polyamide wherein at least a portion of the side chains along a backbone forming the polyamide are amino substituted alkyl chains. See FIGS. 2A and 2B (wherein $R_1$ includes an amino group). The process for producing this polyamide involves reacting a monomer selected from unsaturated carboxylic acids, esters of unsaturated carboxylic acids, anhydrides of unsaturated carboxylic acids and mixtures thereof with a first amine to form an intermediate reaction product in the reaction mixture, wherein the first amine is selected from $RR_1NH$, $RNH_2$, $RR_1NH_2^+$, $RNH_3^+$ and mixtures thereof, wherein R and $R_1$ can be the same or different and each contain between about 1 and 50 carbon atoms and are optionally substituted with heteroatoms oxygen, nitrogen, sulfur, and phosphorus and combinations thereof. The reaction of the monomer and the first amine forms an intermediate reaction product in the reaction mixture. The intermediate reaction product is then reacted with a second amine selected from $R_2R_3NH$, $R_2NH_2$, $R_2R_3NH_2^+$, $R_2NH_3^+$ and mixtures thereof, wherein $R_2$ and $R_3$ can be the same or different and each contain an amino group (—NRH, —$NH_2$, —$NRH_2^+$, —$NH_3^+$) and each contain between about 1 and 50 carbon atoms and are optionally substituted with heteroatoms oxygen, nitrogen, sulfur, and phosphorus and combinations thereof. The reaction of the intermediate reaction product with the second amine forms the polyamide in the reaction mixture. The polyamide may then be separated from the reaction mixture. A polyamide produced in accordance with the method of the invention includes multiples of the R, $R_1$, $R_2$, and $R_3$ groups in vertically aligned spaced relationships along a backbone formed by the polyamide.

Suitable unsaturated carboxylic acids, esters of unsaturated carboxylic acids, and anhydrides of unsaturated carboxylic acids for use as the monomer in this polymerization process have for example from 3 to 18 carbon atoms in the molecule. Of this group of acids, the monocarboxylic acid, acrylic acid, and the dicarboxylic acid, maleic acid, are preferred. Of this group of esters, maleic acid monoesters are preferred. A non-limiting example of anhydrides of the unsaturated carboxylic acids is maleic anhydride. In one example embodiment of the invention, R, $R_1$, $R_2$, and $R_3$ may be selected from alkyl, alkenyl, alkynyl, cycloalkyl, aryl, aralkyl, hydroxyl, nitrile, carboxyl, sulfate, phosphate, sulfonyl, trialkylammonium and combinations thereof and optionally can be substituted with a halogen selected from the group consisting of chlorine, iodine, bromine, fluorine and combinations thereof. The R, $R_1$, $R_2$, and $R_3$ groups may be the same or different depending on the desired structure for the final polyamide. In other words, the first amine and the second amine used in the polymerization process may be the same or different.

The crosslinking agent used in the coating contains at least two functional groups capable of reacting with the amino groups of the polymer used in the coating. It has been discovered that the polymer can be crosslinked using a phosphine crosslinking agent having the general formula $(A)_3P$ and mixtures thereof, wherein A is hydroxyalkyl. The A groups of the phosphine crosslinking agent undergo a spontaneous Mannich-type reaction with amino groups on the polymer under mild conditions (pH~7, aqueous or organic media, room temperature, 2–24 hours). This results in the formation of an aminomethyl-phosphine linkage (N—$CH_2$—P—$CH_2$—N) which is much less susceptible to enzyme deactivation and hydrolysis at a low pH than other known crosslinkages. In addition, the phosphine crosslinking agent offers the benefits of operational simplicity, good biocompatibility, and low cost. The phosphine crosslinking agent can also react with the substrate to create tightly bound anchors between the polyamide coating and the substrate. Non-limiting examples of phosphine crosslinking agents include tris(hydroxymethyl)phosphine, tris(1-hydroxyethyl) phosphine, and tris(1-hydroxypropyl)phosphine. In certain circumstances, it may be cost effective to form the phosphine crosslinking agent in situ such as by the reaction of tetrakis-(hydroxymethyl)phosphonium chloride and triethylamine.

The amount of phosphine crosslinking agent and the amount of polymer used to produce the antimicrobial polymeric composition can be varied depending upon the particular crosslinking agent utilized, the reaction conditions and the particular product application contemplated. Typically, the ratio of A groups in the phosphine crosslinking agent to the total of amount of amino groups in the polyamide can be varied to achieve a predetermined level of crosslinking. Typically, the A groups in the phosphine crosslinking agent to the total of amount of amino groups in the polymer is about 30% to provide acceptable crosslinking. In one version of the invention, enough phosphine crosslinking agent is added to the polyamide such that at least 30% of the available amino groups in the polymer are crosslinked by the A groups in the phosphine crosslinking agent. This percentage or amount of phosphine crosslinker can be varied to obtain antimicrobial polymeric composition coatings with the desired crosslink density.

The metallic antimicrobial agent used in the polymeric composition may be selected from metals, metal alloys, metal salts, metal complexes and mixtures thereof. Preferably, the metallic antimicrobial agent is a metal, metal alloy, metal salt, metal complex, or mixture thereof, which is bactericidal or bacteriostatic. Non-limiting illustrative antimicrobial agents may be selected from chelated silver ions, silver metal, chelated copper ions, copper metal, chelated zinc ions, zinc metal, and mixtures thereof. The amount and/or type of the antimicrobial agent used will vary depending on the particular material employed and ultimate desired effect. For instance, the amount and/or type of the antimicrobial agent which is used in a particular application may vary depending on the type and amount of contamination which is likely to occur and the size of the antimicrobial surface present in the article. For example, certain metals may be highly effective against most bacteria, but less effective against other bacteria. One example level of the antimicrobial agent is from about 4 grams to 12 grams of silver salt to 1.0 to 1.5 grams of the polymeric composition.

The antimicrobial polymeric composition may be applied to any substrate that is considered useful in applications where antimicrobial properties are advantageous. For instance, an article having antimicrobial properties and useful as a medical device may include a substrate comprising a polymeric material conventionally used to fabricate articles commonly used in contact with bodily fluids. In this example, suitable polymeric material may be selected from polyolefins, polyacrylics, polyvinyl chloride, polyamides, polyurethanes, polyurethaneureas, silicone urethane copolymers, polyvinylpyrrolidone, polyvinyl alcohols, cellulosic materials, polystyrene, polyesters, fluorinated polymers, silicone polymers, natural rubber, polycarbonates, and mixtures thereof. The particular substrate selected does not constitute a critical aspect of the invention other than to serve as a support substrate for the antimicrobial polymeric coating composition.

An article having a antimicrobial surface according to the invention may be prepared generally as follows. First, the substrate is precleaned, if necessary, and the surface of the substrate is modified via coupling agent, if necessary. A solution of the polymer having side chains along a backbone forming the polymer wherein at least two of the side chains contain an amino group (—NRH, —NH$_2$, —NRH$_2^+$, —NH$_3^+$) is then prepared in a suitable solvent, such as isopropanol. The polymer concentration can vary and is typically from 1 to 5% depending on the desired coating concentration and final volume of antimicrobial coating desired. A metallic antimicrobial agent selected from metals, metal alloys, metal salts, metal complexes and mixtures thereof is then added to the polymer solution and stirred until the metallic antimicrobial agent dissolves. Without intending to be bound by theory, it is believed that the metal ions form a complex with the polymer, which acts as a chelating agent. The word "complex" indicates some form of bonding wherein the antimicrobial agent is incorporated on, or with, the polymer in such as manner to provide slow release of the antimicrobial agent.

Once the metallic antimicrobial agent has completely dissolved into the polymer solution, a crosslinking agent containing at least two functional groups capable of reacting with the amino groups of the polymer (e.g., tris (hydroxymethyl)phosphine or intermediates which react to form tris(hydroxymethyl)phosphine) is added. Care is taken not to heat this solution as premature crosslinking is undesirable. The polymer/crosslinking agent/metallic antimicrobial agent solution is applied to a substrate and the substrate may be heated or baked in an oven at 125° C. for four hours to complete the crosslinking process and create a crosslinked antimicrobial polymeric composition coating on the substrate. This step may be repeated if necessary. Typically, the coatings are applied using a dipping process. However, the coatings can be spin coated, brushed, sprayed, sponged, or the like onto the substrate.

The reaction between the polyamide, the crosslinking agent, and the metallic antimicrobial agent can be conducted in aqueous and organic phases. Considering the solvent ability, the compatibility with the substrate and reagents, the boiling point, the miscibility with other solvents, and safety factors, isopropanol is one preferred solvent for the coating procedure. In order to provide a smooth crosslinking under optimum stoichiometry, an example concentration ratio for the reactants is: Polymer:Crosslinking Agent=1:0.15 w/w % to 1:0.4 w/w %. Higher concentrations of tris (hydroxymethyl)phosphine may lead to an extremely short pot life by precipitation of the crosslinked materials from solution. Accordingly, a suitable concentration ratio for the reactants is: Polymer: Crosslinking agent=1000 milligrams:440 milligrams.

EXAMPLES

The following examples serve to further illustrate the invention. The Comparative Example details the preparation of a substrate having a crosslinked polyamide coating. Examples 1–6 detail the preparation of substrates having different antimicrobial crosslinked polyamide coatings in accordance with the invention. The examples are not intended to limit the invention in any way.

Comparative Example

Preparation of Substrates Having A Crosslinked Polyamide Coating

A polymer with side chains was prepared as follows. First, 1.0 moles (144.1 grams) of maleic acid mono-ethyl ester was dissolved in 100 grams of isopropanol in a break away resin kettle. The kettle containing the maleic acid mono-ethyl ester/isopropanol solution was then cooled in an ice bath with agitation. Second, 0.5 moles (160.7 grams) of commercially available tetradecylamine was dissolved in 250 grams of isopropanol and added slowly to the cooled maleic acid mono-ethyl ester solution with stirring. A Michael-type addition reaction product began to precipitate within 5 minutes. The tetradecylamine addition required about two hours with ice bath conditions being maintained throughout. Third, 58.1 grams (0.25 moles) of commercially available pentaethylenehexamine were added drop wise to the reaction solution over a two hour period. The reaction is removed from the ice bath at the end of the monomer addition and stirred for an additional 2 hours. The amount of pentaethylenehexamine charged is determined from the monomer charge from the formation of intermediate. After complete addition of the pentaethylene-hexamine, the reaction kettle was removed from the cold bath with continuous stirring for another 2 hours. A 2.5% solution of the polymer with side chains was then prepared in isopropanol. One milliliter of triethylamine was then added to the solution under stirring. Two milliliters of glutaraldehyde were then added to the solution. A 0.15 milliliter portion of tetrakis-(hydroxymethyl) phosphonium chloride was then added to the solution followed by 0.3 milliliters of dioctyl sebacate. The polymer solution was then applied to a 10 millimeter by 10 millimeter polydimethylsiloxane substrate and a 10 millimeter by 10 millimeter polypropylene substrate. In doing so, the substrates were dipped into the polymer solution and removed after 0.5 to 2 minutes. Each wet substrate was dried and cured by hot air at 120° C.–150° C. for 1 minute. The dip-and-dry operation can be repeated one or more times when a higher thickness is required. The coated substrates were then placed in an oven at 125° C. for four hours.

Example 1

Preparation of a Substrate with a Polyamide Coating Including Silver

Example 1a

Preparation of A Polyamide with Side Chains

A polymer with side chains was prepared as follows. First, 1.0 moles (144.1 grams) of maleic acid mono-ethyl ester was dissolved in 100 grams of isopropanol in a break away resin kettle. The kettle containing the maleic acid monoethyl ester/isopropanol solution was then cooled in an ice bath with agitation. Second, 0.5 moles (160.7 grams) of commercially available tetradecylamine was dissolved in 250 grams of isopropanol and added slowly to the cooled maleic acid mono-ethyl ester solution with stirring. A Michael-type addition reaction product began to precipitate within 5 minutes. The tetradecylamine addition required about two hours with ice bath conditions being maintained throughout. Third, 58.1 grams (0.25 moles) of commercially available pentaethylenehexamine were added drop wise to the reaction solution over a two hour period. The reaction is removed from the ice bath at the end of the monomer addition and stirred for an additional 2 hours. The amount of pentaethylene-hexamine charged is determined from the monomer charge from the formation of intermediate. After complete addition of the pentaethylene—hexamine, the reaction kettle was removed from the cold bath with continuous stirring for another 2 hours.

Example 1b

Preparation of an Antimicrobial Polymer Solution from Example 1a Polymer

A 2.5% solution of the polymer of Example 1a was prepared in isopropanol. Then, 10 grams of silver pentaflouropropionate were added to 50 milliliters of the 2.5% polymer solution. The solution was then stirred until the silver pentaflouropropionate completely dissolved. The solution darkened and became very dark brown or black after 2 or 3 hours. One milliliter of triethylamine was then added to the solution under stirring. Two milliliters of glutaraldehyde were then added to the solution. A 0.15 milliliter portion of tetrakis-(hydroxymethyl) phosphonium chloride was then added to the solution followed by 0.3 milliliters of dioctyl sebacate.

Example 1c
Preparation of a Substrate with an Antimicrobial Polymer Coating

The polymer solution prepared in Example 1b was applied to a 10 millimeter by 10 millimeter polydimethylsiloxane substrate and a 10 millimeter by 10 millimeter polypropylene substrate. In doing so, the substrates were dipped into the solution and removed after 0.5 to 2 minutes. Each wet substrate was dried and cured by hot air at 120° C.–150° C. for 1 minute. The dip-and-dry operation can be repeated one or more times when a higher thickness is required. The coated substrates were then placed in an oven at 125° C. for four hours.

Example 2
Preparation of a Substrate with Polyamide Coating Including Copper

Example 2a
Preparation of A Polyamide with Side Chains

A polymer with side chains was prepared as detailed in Example 1a.

Example 2b

Preparation of an Antimicrobial Polymer Solution from Example 2a Polymer

A 10 gram sample of the polymer of Example 2a was dissolved in isopropanol. Eight grams of copper 2-ethylhexanoate were then added to the polymer solution, and the resulting polymer—copper salt solution was stirred until it became a dark greenish brown color in about 3 hours. It is believed that the color developed from the green to aqua blue of the salt to form the dark green/brown complex of the polymer with the copper ion. The polymer-copper complex was rotovapped to dryness, and thereafter rotovapped and dried in a vacuum oven to remove the last traces of isopropanol. Two grams of the polymer-copper complex were then added to 50 milliliters of a 2.5% solution of the polymer of Example 2a in isopropanol. Seven grams of #200 mesh copper powder were then added to the solution. One milliliter of triethylamine was then added to the solution under stirring. Two milliliters of glutaraldehyde were then added to the solution. A 0.2 milliliter portion of tetrakis-(hydroxymethyl) phosphonium chloride was then added to the solution followed by 0.2 milliliters of dioctyl sebacate.

Example 2c

Preparation of a Substrate with an Antimicrobial Polymer Coating

The polymer solution prepared in Example 2b was applied to a 10 millimeter by 10 millimeter polydimethylsiloxane substrate and a 10 millimeter by 10 millimeter polypropylene substrate. In doing so, the substrates were dipped into the solution and removed after 0.5 to 2 minutes. Each wet substrate was dried and cured by hot air at 120° C.–150° C. for 1 minute. The dip-and-dry operation can be repeated one or more times when a higher thickness is required. The coated substrates were then placed in an oven at 125° C. for four hours.

Example 3
Preparation of a Substrate with a Polyamide Coating Including Zinc

Example 3a
Preparation of A Polyamide with Side Chains

A polymer with side chains was prepared as detailed in Example 1a.

Example 3b

Preparation of an Antimicrobial Polymer Solution from Example 3a Polymer

A 2.5% solution of the polymer of Example 3a was prepared in isopropanol. Then, 5 grams of zinc acetate were added to 50 milliliters of the 2.5% polymer solution. The solution was then stirred until the zinc acetate completely dissolved. One milliliter of triethylamine was then added to the solution under stirring. Two milliliters of glutaraldehyde were then added to the solution. A 0.2 milliliter portion of tetrakis-(hydroxymethyl) phosphonium chloride was then added to the solution followed by 0.3 milliliters of dioctyl sebacate.

Example 3c
Preparation of a Substrate with an Antimicrobial Polymer Coating

The polymer solution prepared in Example 3b was applied to a 10 millimeter by 10 millimeter polydimethylsiloxane substrate and a 10 millimeter by 10 millimeter polypropylene substrate. In doing so, the substrates were dipped into the solution and removed after 0.5 to 2 minutes. Each wet substrate was dried and cured by hot air at 120° C.–150° C. for 1 minute. The dip-and-dry operation can be repeated one or more times when a higher thickness is required. The coated substrates were then placed in an oven at 125° C. for four hours.

Example 4
Preparation of a Substrate with a Polyamide Coating Base Including Copper and A Polyamide Overcoat Including Silver The polymer solution prepared in Example 2b was applied to a 10 millimeter by 10 millimeter polydimethylsiloxane substrate and a 10 millimeter by 10 millimeter polypropylene substrate forming the copper base coat. In doing so, each substrate was dipped into the solution and removed after 0.5 to 2 minutes. Each wet substrate was dried and cured by hot air at 120° C.–150° C. for 1 minute. The polymer solution prepared in Example 1 b was then applied to the coated polydimethylsiloxane substrate and the coated polypropylene substrate forming the silver overcoat. In doing so, each substrate was dipped into the solution and removed after 0.5 to 2 minutes. The coated substrates were then placed in an oven at 125° C. for four hours. This produced polydimethylsiloxane and polypropylene substrates having a polymer coating base including copper and a polymer overcoat including silver.

Example 5
Preparation of a Substrate with a Polyamide Coating Base Including Copper and A Polyamide Overcoat Including Zinc The polymer solution prepared in Example 2b was applied to a 10 millimeter by 10 millimeter polydimethylsiloxane substrate and a 10 millimeter by 10 millimeter polypropylene substrate. In doing so, each substrate was dipped into the solution and removed after 0.5 to 2 minutes. Each wet substrate was dried and cured by hot air at 120° C.–150° C. for 1 minute. The polymer solution prepared in Example 2b was then applied to the coated polydimethylsiloxane substrate and the coated polypropylene substrate. In doing so, each substrate was dipped into the solution and removed after 0.5 to 2 minutes. The coated substrates were then placed in an oven at 125° C. for four hours. This produced polydimethylsiloxane and polypropylene substrates having a polymer coating base including copper and a polymer overcoat including zinc.

Example 6
Preparation of a Substrate with a Polyamide Coating Base Including Silver and A Polyamide Overcoat Including Copper The polymer solution prepared in Example 1b was applied to a 10 millimeter by 10 millimeter polydimethylsiloxane substrate and a 10 millimeter by 10 millimeter polypropylene substrate. In doing so, each substrate was dipped into the solution and removed after 0.5 to 2 minutes. Each wet substrate was dried and cured by hot air at 120° C.–150° C. for 1 minute. The polymer solution prepared in Example 2b was applied to the coated polydimethylsiloxane substrate and the coated polypropylene substrate. In doing so, each substrate was dipped into the solution and removed after 0.5 to 2 minutes. The coated substrates were then placed in an oven at 125° C. for four hours. This produced polydimethylsiloxane and polypropylene substrates having a polymer coating base including silver and a polymer overcoat including copper.

Example 7
Antimicrobial Activity Assay

The selection of target microorganisms for examining the antimicrobial activity of the coated polydimethylsiloxane substrates and the coated polypropylene substrates produced in the Comparative Example and Examples 1c, 2c, 3c, 4, 5 and 6 was based on the potential human pathogenic microorganisms, which include gram positive bacteria, *Bacillus subtilis* and *Staphylococcus aureus*; gram negative bacteria, *E. coli* and *Pseudomonas aeruginosa*; and yeast, *Candida albicans*. Broth cultures were prepared for each microorganism. Bacteria, *Bacillus subtilis, Staphylococcus aureus, E. coli* and *Pseudomonas aeruginosa* were grown in 50 milliliters of sterile tryptic soy broth in 500 milliliter baffle flask at 200 rpm. The cultures were grown at 37° C. overnight, and used for antimicrobial activity assay plates and stock culture. The yeast, Candida albicans was cultivated in 50 milliliters of sterile yeast malt broth in 250 milliliter baffle flask at 25–28° C. for 1 day and used for the activity assay plates and stock culture.

Antimicrobial activity assay plates were then prepared. Yeast malt agar and tryptic soy agar were autoclaved for 20 minutes. The sterile molten agar was allowed to cool to 42–45° C. The prepared broth cultures of the target microorganisms were inoculated to a final concentration of 5% (v/v). The broth cultures were mixed to obtain a homogeneous suspension, and a 20 milliliter aliquot of culture mixed agar media was poured into sterile plastic petri dishes. The agar was allowed to solidify, and dishes not to be used immediately were stored at 4° C.

The coated polydimethylsiloxane substrates and the coated polypropylene substrates produced in the Comparative Example and Examples 1c, 2c, 3c, 4, 5 and 6 were placed on the prepared agar plates. After incubation at 30° C. for *C. albicans* and 37° C. for the other microorganisms, respectively for 1–2 days, a clear zone of growth inhibition surrounding the coated substrates was visible against a partially opaque background of growth. The degree of inhibition was scored using the following point system shown in Table 1. (When the inhibition zone was hazy, the inhibition grade was ranked one lower degree.) The results are shown in Table 2.

TABLE 1

| Score | Score Description |
|---|---|
| 0 | No inhibition. |
| ½ | Inhibition, but, not clearly measurable. |
| 1 | Clearly observable inhibition wherein the diameter of the inhibition zone is in the range of 11–13 millimeters. |
| 1½ | Half of a degree between 1 and 2. |
| 2 | Clearly observable inhibition wherein the diameter of the inhibition zone is in the range of 14–16 millimeters. |
| 3 | Clearly observable inhibition wherein the diameter of the inhibition zone is in the range of 17–20 millimeters. |
| 4 | Clearly observable inhibition wherein the diameter of the inhibition zone is over 21 millimeters. |

TABLE 2

| Test No. | Example Tested | *Staphylococcus aureus* | *Pseudomonas aeruginosa* | *Candida albicans* | *E. coli* | *Bacillus subtilis* |
|---|---|---|---|---|---|---|
| 1 | Comparative Example | 0 | 0 | 0 | 0 | 0 |
| 2 | Example 2c | 1 | ½ | ½ | 1 | 2 |
| 3 | Example 1c | ½ | 0 | ½ | 0 | 3 |
| 4 | Example 4 | 1½ | 2 | 1 | 2 | 3 |

TABLE 2-continued

| Test No. | Example Tested | Staphylococcus aureus | Pseudomonas aeruginosa | Candida albicans | E. coli | Bacillus subtilis |
|---|---|---|---|---|---|---|
| 5 | Example 3c | 0 | 0 | 0 | 0 | 1 |
| 6 | Example 5 | 1½ | 1½ | 1 | 1 | 2 |
| 7 | Example 4 | 2 | 2 | 1½ | 1 | 3 |
| 8 | Example 6 | 0 | 1 | ½ | 0 | ½ |
| 9 | Example 1c | 0 | ½ | 1 | 0 | ½ |

Analysis

Upon review of the results for the inhibitory activity of the coated polydimethylsiloxane substrates and the coated polypropylene substrates produced in the Comparative Example and Examples 1c, 2c, 3c, 4, 5 and 6 against bacterial/microbial growth as shown in Table 2, many trends can be seen. Among the series of antimicrobials tested, the coatings including two metals (i.e., galvanic coatings) demonstrated the highest activity, both in the ability to suppress the colonization and its promising spectrum of action. The polymer coatings including a single metal also show significant progress and offer the same advantages as the galvanic coating. The single metal coatings show good activity; however, the activity is less than that of the galvanic coatings.

It is believed that the mode of metal chelation is likely to contribute significantly to the results of the bioassay. Ionic interaction can offer higher concentrations of the active component in the incubation media. Meanwhile, immobilization by entrapping the antimicrobial(s) in the bulk polymer coating would be expected to show a more durable time of action.

It has also been discovered that the approach of the present invention in incorporating the metal into the polymer coating is quite advantageous and unexpected. The polymer used in the coating serves to strongly chelate the metal. Without intending to be bound by theory, it is believed that the polymer structure can be viewed as that of an amino analogue of a crown ether. The coatings formed are more durable than vapor deposited films used in existing commercial products and contain the antimicrobial agent throughout the coating thereby providing a controlled release of the antimicrobial agent for several weeks.

Therefore, it can be seen that this work has provided an improved antimicrobial polymeric composition that may be easily applied as a coating to a substrate to provide an article which has excellent antimicrobial properties. The antimicrobial polymeric composition has several coating applications including, without limitation, medical devices, antifouling applications for aqueous and marine environments, and corrosion control.

Although the present invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A polymeric composition having antimicrobial properties, the polymeric composition comprising: a crosslinked chemical combination of (i) a polymer having side chains along a backbone forming the polymer, at least two of the side chains containing an amino group, (ii) an antimicrobial agent selected from the group consisting of metals, metal alloys, metal salts, metal complexes and mixtures thereof, and (iii) a crosslinking agent containing at least two functional groups capable of reacting with the amino groups;

wherein the polymer is a polyamide, and the polyamide is synthesized by (i) reacting a monomer selected from the group consisting of unsaturated carboxylic acids, esters of unsaturated carboxylic acids, anhydrides of unsaturated carboxylic acids, and mixtures thereof, and a first amine to form an intermediate reaction product, wherein the first amine is selected from the group consisting of $RR_1NH$, $RNH_2$, polyalkylene polyamines and mixtures thereof, and (iii) reacting the intermediate reaction product and a second amine to form the polyamide, wherein the second amine is selected from the group consisting of $R_2R_3NH$, $R_2NH$, polyalkylene polyamines and mixtures thereof, wherein R, $R_1$, $R_2$, and $R_3$ are the same or different and each R, $R_1$, $R_2$ and $R_3$ contains between 1 and 50 carbon atoms and is optionally substituted with heteroatoms oxygen, nitrogen, sulfur, phosphorus, or combinations thereof: and at least one of the selected amines includes at least two amino groups.

2. The polymeric composition of claim 1 wherein R and $R_1$ are alkyl.

3. The polymeric composition of claim 2 wherein the amine comprises tetradecylamine.

4. The polymeric composition of claim 1 wherein the second amine comprises a polyalkylene polyamine.

5. The polymeric composition of claim 4 wherein the polyalkylene polyamine comprises pentaethylenehexamine.

6. The polymeric composition of claim 1 wherein monomer is selected from the group consisting of unsaturated dicarboxylic acids, esters of unsaturated dicarboxylic acids, anhydrides of unsaturated dicarboxylic acids, and mixtures thereof.

7. The polymeric composition of claim 6 wherein the monomer is selected from the group consisting of maleic anhydride, maleic acid esters, and mixtures thereof.

8. The polymeric composition of claim 7 wherein the first amine comprises tetradecylamine.

9. The polymeric composition of claim 7 wherein the second amine comprises a polyalkylene polyamine.

10. The polymeric composition of claim 9 wherein the polyalkylene polyamine comprises pentaethylenehexamine.

11. The polymeric composition of claim 6, wherein the antimicrobial agent is selected from the group consisting of chelated silver ions, silver metal, chelated copper ions, copper metal, chelated zinc ions, zinc metal and mixtures thereof.

12. The polymeric composition of claim 7 wherein the antimicrobial agent is selected from the group consisting of chelated silver ions, silver metal, chelated copper ions, copper metal, chelated zinc ions, zinc metal and mixtures thereof.

13. The polymeric composition of claim 1 wherein the antimicrobial agent is selected from the group consisting of chelated silver ions, silver metal, chelated copper ions, copper metal, chelated zinc ions, zinc metal and mixtures thereof.

14. The polymeric composition of claim 1 wherein the monomer comprises a maleic acid ester.

15. The polymeric composition of claim 1 wherein the monomer comprises maleic anhydride.

16. The polymeric composition of claim 1 wherein the crosslinking agent is selected from the group consisting of phosphines having the formula $(A)_3P$, wherein A is hydroxyalkyl, and mixtures thereof.

17. The polymeric composition of claim 16 wherein the crosslinking agent is tris(hydroxymethyl)phosphine.

18. The polymeric composition of claim 1, further comprising a second crosslinked chemical combination of (i) a second polymer having side chains along a backbone forming the second polymer, at least two of the side chains containing an amino group, (ii) a second antimicrobial agent selected from the group consisting of metals, metal alloys, metal salts, metal complexes and mixtures thereof, and (iii) a second crosslinking agent containing at least two functional groups capable of reacting with the amino groups, wherein the antimicrobial agent and the second antimicrobial agent are different.

19. The polymeric composition of claim 18 wherein the second polymer is a polyamide, and the polyaxmde is synthesized by reacting a monomer selected from the group consisting of unsaturated carboxylic acids, esters of unsaturated carboxylic acids, anhydrides of unsaturated carboxylic acids, and mixtures thereof, and an amine, wherein the amine is selected from the group consisting of $RR_1NH$, $RNH_2$, polyalkylene polyamines and mixtures thereof, wherein the R and $R_1$ groups are the same or different and each contain between about 1 and 50 carbon atoms and are optionally substituted with heteroatoms oxygen, nitrogen, sulfur, and phosphorus and combinations thereof, wherein at least one of the selected amines includes at least two amino groups.

20. The polymeric composition of claim 18 wherein: the crosslinking agent and the second crosslinking agent are selected from the group consisting of phosphines having the formula $(A)_3P$, wherein A is hydroxyalkyl, and mixtures thereof.

21. The polymeric composition of claim 18 wherein: the antimicrobial agent is selected from the group consisting of chelated copper ions, copper metal, and mixtures thereof, and the second antimicrobial is selected from the group consisting of chelated silver ions, silver metal, and mixtures thereof.

22. The polymeric composition of claim 18 wherein: the antimicrobial agent is selected from the group consisting of chelated copper ions, copper metal, and mixtures thereof, and the second antimicrobial is selected from the group consisting of chelated zinc ions, zinc metal, and mixtures thereof.

23. A polyamide material comprising:
(A) a crosslinked polymeric material formed by a process comprising:
(i) reacting a reaction mixture comprising a monomer selected from the group consisting of maleic anhydride, maleic acid esters, and mixtures thereof, and one or more amines selected from polyalkylene polyamines and amines having the formula $R-NH_2$ to form an intermediate reaction product, wherein the R group contains between 1 and 50 carbon atoms and is optionally substituted with heteroatoms oxygen, nitrogen, sulfur, phosphorus, and combinations thereof; wherein at least one of the selected amines includes at least two amino groups; and
(ii) reacting the intermediate reaction product and the one or more amines to form a polyamide; and
(iii) reacting the polyamide with a crosslinking agent to from a crosslinked polymer, wherein the crosslinking agent includes at least two functional groups capable of reacting with amino groups; and
(B) copper ions, copper metal, or a mixture thereof.

24. The polyamide material of claim 23, wherein the selected amines comprise tetradecylamine and pentaethylenehexamine.

25. A polyamide material comprising:
(A) a polymer formed by a process comprising:
(i) reacting a reaction mixture comprising a monomer selected from the group consisting of unsaturated carboxylic acids, esters of unsaturated carboxylic acids, anhydrides of unsaturated carboxylic acids, and mixtures thereof, and one or more amines selected from polyalkylene polyamines and amines having the formula $R-NH_2$ to form an intermediate reaction product, wherein the R group contains between 1 and 50 carbon atoms and is optionally substituted with heteroatoms oxygen, nitrogen, sulfur, phosphorus, and combinations thereof, wherein at least one of the selected amines includes at least two amino groups; and
(ii) reacting the intermediate reaction product and the one or more amines to form a polyamide; and
(B) an antimicrobial agent selected from the group consisting of a metal, a metal alloy, a metal salt, a metal complex, and mixtures thereof.

26. A polyamide material comprising:
(A) a crosslinked polymeric material formed by a process comprising:
(i) reacting a reaction mixture comprising a monomer selected from the group consisting of unsaturated carboxylic acids, esters of unsaturated carboxylic acids, anhydrides of unsaturated carboxylic acids, and mixtures thereof, and one or more amines selected from polyalkylene polyamines and amines having the formula $R-NH_2$ to form an intermediate reaction product, wherein the R group contains between 1 and 50 carbon atoms and is optionally substituted with heteroatoms oxygen, nitrogen, sulfur, phosphorus, and combinations thereof, wherein at least one of the selected amines includes at least two amino groups; and
(ii) reacting the intermediate reaction product and the one or more amines to form a polyamide; and
(iii) reacting the polyamide with a crosslinking agent to from a crosslinked polymer, wherein the crosslinking agent includes at least two functional groups capable of reacting with amino groups; and
(B) an antimicrobial agent selected from the group consisting of a metal, a metal alloy, a metal salt, a metal complex, of and mixtures thereof.

27. The polyamide material of claim 26 wherein the monomer comprises at least one unsaturated carboxylic monomer selected from the group consisting of maleic anhydride, maleic acid esters, and mixtures thereof.

28. The polyamide material of claim 26 wherein the antimicrobial agent includes chelated silver ions, silver metal, chelated copper ions, copper metal, chelated zinc ions, zinc metal, or mixtures thereof.

29. A crosslinked polymeric material formed from:
(A) a polyamide formed from a mixture which comprises:
(i) one or more monomers selected from the group consisting of maleic anhydride, maleic acid esters, and mixtures thereof; and (ii) one or more amines selected from the group consisting of R-NH$_2$, a polyalkylene polyamine, and mixtures thereof, wherein the R group R-contains between 1 and 50 carbon atoms and is optionally substituted with heteroatoms oxygen, nitrogen, sulfur, phosphorus, or combinations thereof; wherein one or more of the selected amines includes at least two amino groups;

(B) one or more antimicrobial agents selected from the group consisting of metals, metal alloys, metal salts, metal complexes and mixtures thereof; and (C) one or more crosslinking agents selected from the group consisting of aliphatic isocyanate compounds having 2 or more —N=C=O groups; aromatic isocyanate compounds having 2 or more —N=C=O groups; aliphatic aldehyde compounds having 2 or more —CHO groups; aromatic aldehyde compounds having 2 or more —CHO groups; phosphines having the general formula (A)$_2$P(B) wherein A is hydroxyalkyl, and B is hydroxyalkyl, alkyl, or amyl; epoxy resins having end groups of the formula:

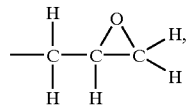

and mixtures thereof.

30. The crosslinked polymeric material of claim 29, wherein the monomer comprises maleic anhydride monoethyl ester.

31. The crosslinked polymeric material of claim 29, wherein the one or more amines comprise tetradecylamine.

32. The crosslinked polymeric material of claim 29, wherein the one or more amines comprise pentaethylenehexamine.

33. The crosslinked polymeric material of claim 29, wherein the one or more antimicrobial agents comprise chelated silver ions, silver metal, or a mixture thereof.

34. The crosslinked polymeric material of claim 29, wherein the one or more antimicrobial agents comprise chelated copper ions, copper metal, or a mixture thereof.

35. The crosslinked polyamide material of claim 29, wherein the one or more crosslinking agents comprise glutaraldehyde.

36. The crosslinked polymeric material of claim 29, wherein the one or more crosslinking agents comprise a phosphine formed from the reaction of tetrakis(hydroxymethyl)phosphonium chloride and triethylamine.

37. The crosslinked polymeric material of claim 29, wherein the one or more crosslinking agents comprise tris(hydroxymethyl)phosphine.

* * * * *

UNITED STATES PATENT AND TRADEMARK OFFICE
CERTIFICATE OF CORRECTION

PATENT NO. : 6,797,743 B2
DATED : September 28, 2004
INVENTOR(S) : William F. McDonald, Stacey C. Wright and Andrew C. Taylor It is certified that error appears in the above-identified patent and that said Letters Patent is hereby corrected as shown below:

Title page,
Item [63], Related U.S. Application Data, delete "09/698,679" and substitute -- 09/698,619 --.

Column 14,
Line 25, preceding "reacting" delete "(iii)" and substitute -- (ii) --.
Line 28, preceding "polyalkylene" delete "$R_2R_3NH, R_2NH$" and substitute -- $R_2R_3NH, R_2NH_2$ -- .
Line 39, preceding "amine" insert -- first --.
Line 58, following "claim" delete "6" and substitute -- 1 --.

Column 15,
Line 1, following "claim" delete "1" and substitute -- 7 --.
Line 28, delete "polyaxmde" and substitute -- polyamide --.

Column 16,
Line 8, delete "from" and substitute -- form -- .
Line 50, delete "from" and substitute -- form --.
Line 55, following "complex," delete "of".

Column 17,
Line 3, preceding "contains" delete "R-".
Line 20, following "alkyl, or" delete "amyl" and substitute -- aryl --.

Signed and Sealed this

Nineteenth Day of April, 2005

JON W. DUDAS
*Director of the United States Patent and Trademark Office*